United States Patent
Ko

(10) Patent No.: US 12,023,511 B2
(45) Date of Patent: Jul. 2, 2024

(54) RF THERAPEUTIC DEVICE AND METHOD FOR CONTROLLING SAME

(71) Applicant: LUTRONIC CORPORATION, Goyang-si (KR)

(72) Inventor: Kwang Chon Ko, Paju-si (KR)

(73) Assignee: LUTRONIC CORPORATION, Goyang-si (KR)

( * ) Notice: Subject to any disclaimer, the term of this patent is extended or adjusted under 35 U.S.C. 154(b) by 409 days.

(21) Appl. No.: 17/419,688

(22) PCT Filed: Dec. 9, 2019

(86) PCT No.: PCT/KR2019/017309
§ 371 (c)(1),
(2) Date: Jun. 29, 2021

(87) PCT Pub. No.: WO2020/141744
PCT Pub. Date: Jul. 9, 2020

(65) Prior Publication Data
US 2022/0080215 A1    Mar. 17, 2022

(30) Foreign Application Priority Data
Dec. 31, 2018 (KR) .................. 10-2018-0173464

(51) Int. Cl.
*A61N 1/40* (2006.01)
*A61N 1/05* (2006.01)
*A61N 1/06* (2006.01)
*A61N 1/08* (2006.01)

(52) U.S. Cl.
CPC ............. *A61N 1/40* (2013.01); *A61N 1/0502* (2013.01); *A61N 1/06* (2013.01); *A61N 2001/083* (2013.01)

(58) Field of Classification Search
None
See application file for complete search history.

(56) References Cited

U.S. PATENT DOCUMENTS

| 10,035,024 | B2 | 7/2018 | Ko | |
| 2009/0093864 | A1* | 4/2009 | Anderson | A61B 18/1477 607/99 |
| 2010/0262135 | A1* | 10/2010 | Berube | A61B 18/1477 606/33 |
| 2013/0012937 | A1* | 1/2013 | Mulier | A61B 18/1477 606/33 |
| 2016/0114181 | A1* | 4/2016 | Vaynberg | A61F 7/007 607/104 |

(Continued)

FOREIGN PATENT DOCUMENTS

| KR | 20030094876 A | 12/2003 |
| KR | 20110000790 A | 1/2011 |

(Continued)

*Primary Examiner* — Michael W Kahelin

(57) ABSTRACT

The present invention relates to an RF therapeutic device and a method for controlling same, the RF therapeutic device comprising: an RF generation unit for generating RF energy; a plurality of RF electrodes connected to the RF generation unit through an RF circuit and selectively inserted into body tissue to transfer the RF energy to the body tissue; and a sensing unit for detecting a loss of the RF energy transferred to the body tissue, the loss resulting from the impedance characteristic of the body tissue.

20 Claims, 8 Drawing Sheets

(56) References Cited

U.S. PATENT DOCUMENTS

| | | |
|---|---|---|
| 2018/0103991 A1* | 4/2018 | Linhart .............. A61B 18/1477 |
| 2018/0133469 A1* | 5/2018 | Palero ...................... A61N 1/06 |
| 2019/0262066 A1 | 8/2019 | Ko et al. |
| 2019/0357971 A1* | 11/2019 | Adi .................... A61B 18/1815 |

FOREIGN PATENT DOCUMENTS

| | | |
|---|---|---|
| KR | 101300123 B1 | 8/2013 |
| KR | 20140090349 A | 7/2014 |
| KR | 20150083582 A | 7/2018 |
| KR | 20180111203 A | 10/2018 |
| KR | 20190102437 A | 9/2019 |
| WO | WO03103768 A1 | 12/2003 |
| WO | WO2018131870 A1 | 7/2018 |
| WO | WO2018182188 A1 | 10/2018 |

* cited by examiner

RF THERAPEUTIC DEVICE AND METHOD FOR CONTROLLING SAME

TECHNICAL FIELD

The disclosure relates to a radio frequency (RF) therapeutic device and a method of controlling the same, and more particularly to an RF therapeutic device and a method of controlling the same, in which treatment is carried out by inserting RF electrodes into a body.

BACKGROUND ART

A tissue treatment method of using radio frequency (RF) energy may be classified into a contact treatment method where tissue is treated by transferring RF energy to the outer surface of the tissue, and an invasive treatment method where an RF electrode is partially or entirely inserted into tissue to transfer the RF energy. Between them, the invasive treatment method generally employs a needle, a catheter or the like therapeutic device having a small-diameter insert, and carries out treatment by inserting the therapeutic device up to a target position inside tissue and then transferring the RF energy to the inside of the tissue.

Such an RF treatment method has been generally used in making an incision, stop bleeding or the like surgical treatment in a lesion of an internal organ. Recently, the RF treatment method has been used for wrinkle removal, scar removal, acne treatment and the like dermal lesion treatment by inserting a needle-type electrode into a skin, and such a technique has also been disclosed in Korean patent publication No. 10-2011-0000790.

Recently, the size of the needle has been gradually decreased to relieve a patients pain, and thus a level of difficulty in uniformly processing RF electrodes provided at an end portion of the needle becomes higher. Therefore, produced RF electrodes are likely to be a little different in quality, but it is difficult for human's eyes to check such difference without individually testing all the produced RF electrodes. The difference in quality between the RF electrodes causes the RF energy to be differently transferred to tissue even though the RF energy of the same power is given, thereby carrying out insufficient treatment or causing unexpected damage to the tissue.

DISCLOSURE

Technical Problem

The disclosure is to provide a radio frequency (RF) therapeutic device and a method of controlling the same, in which RF electrodes of defective processing or RF electrodes of undesired specifications are detected and supplied with appropriate RF energy to have normal therapeutic effects even though such RE electrodes are used in treatment based on the RF energy.

Technical Solution

To achieve the object of the disclosure, there is provided a radio frequency (RF) therapeutic device including: an RF generator configured to generate RF energy; an insert formed with an RF electrode at an end portion thereof, and configured to be selectively inserted in body tissue and transfer the RF energy to the body tissue: a sensor configured to measure impedance while the RF energy is being transferred to the body tissue and obtain information about the RF electrode; and a controller configured to adjust parameters of the RF energy based on a detection result of the sensor.

The controller may be configured to compare the measured impedance with reference impedance corresponding to the RF electrode, and adjust the parameters of the RF energy based on a comparison result. Specifically, the controller may be configured to control the RF energy transferred to the RF electrode to be decreased when the measured impedance is higher than the reference impedance, but control the RF energy transferred to the RF electrode to be increased when the measured impedance is lower than the reference impedance.

Further, the controller may be configured to inform a user that the insert is defective when the measured impedance goes beyond a reference impedance section for the RF electrode. Further, the controller may be configured to control the RF energy not to be transferred to the RF electrode when the measured impedance goes beyond the reference impedance section for the RF electrode.

Furthermore, the RF therapeutic device may further include an identifier configured to identify length information about the RF electrode based on impedance measured by the sensor.

The RF generator may be configured to selectively generate test. RF energy used in obtaining information about the RF electrode and treatment. RF energy used in treating body tissue. The test. RF energy may include lower power than the treatment RF energy.

The controller may be configured to identify parameters of the treatment RF energy based on impedance information detected by transferring the test RF energy at an initial insertion position, and control the RF generator to transfer the treatment RF energy having the identified parameters to at a subsequent insertion position.

Meanwhile, the insert may be replaceably provided, and the controller may be configured to identify whether the insert matches a set model based on a detection result of the sensor.

The insert may include a plurality of microneedles, each microneedle includes a body including an insulating material on a surface thereof, and the RF electrode may include a conductive material formed at an end portion of the body. The microneedle may include a cross-sectional diameter of 100 to 500 µm, and the electrode portion includes a length of 0.1 to 1 mm.

Meanwhile, the object of the disclosure may be achieved by a method of controlling a RF therapeutic device, including: positioning a handpiece at a first position; inserting an insert at the first position and transferring RF energy; obtaining information about an RF electrode by measuring impedance while the RF energy is being transferred; identifying parameters of the RF energy based on the obtained information; positioning the handpiece at a second position; and transferring the RF energy including the identified parameters.

Here, the identification of the parameters of the RF energy may include comparing the measured impedance with reference impedance corresponding to the RF electrode, and identifying the parameters of the RF energy based on a comparison result.

Further, the RF energy transferred to the first position may include test RF energy, and the RF energy transferred to the second position includes treatment. RF energy, and the test RF energy may include lower power than the treatment RF energy.

The obtainment of the information about the RF electrode by measuring impedance while the RF energy is being transferred may include identifying length information about the RF electrode, and the parameters of the RF energy may be identified based on the length information of the RF electrode.

Advantageous Effects

According to the disclosure, radio frequency (RF) energy to be transferred is adjusted to carry out treatment even when RF electrodes are different in a processing error, thereby preventing unexpected tissue damage and carrying out treatment with uniform quality

MODE FOR CARRYING OUT DISCLOSURE

Figure 1:
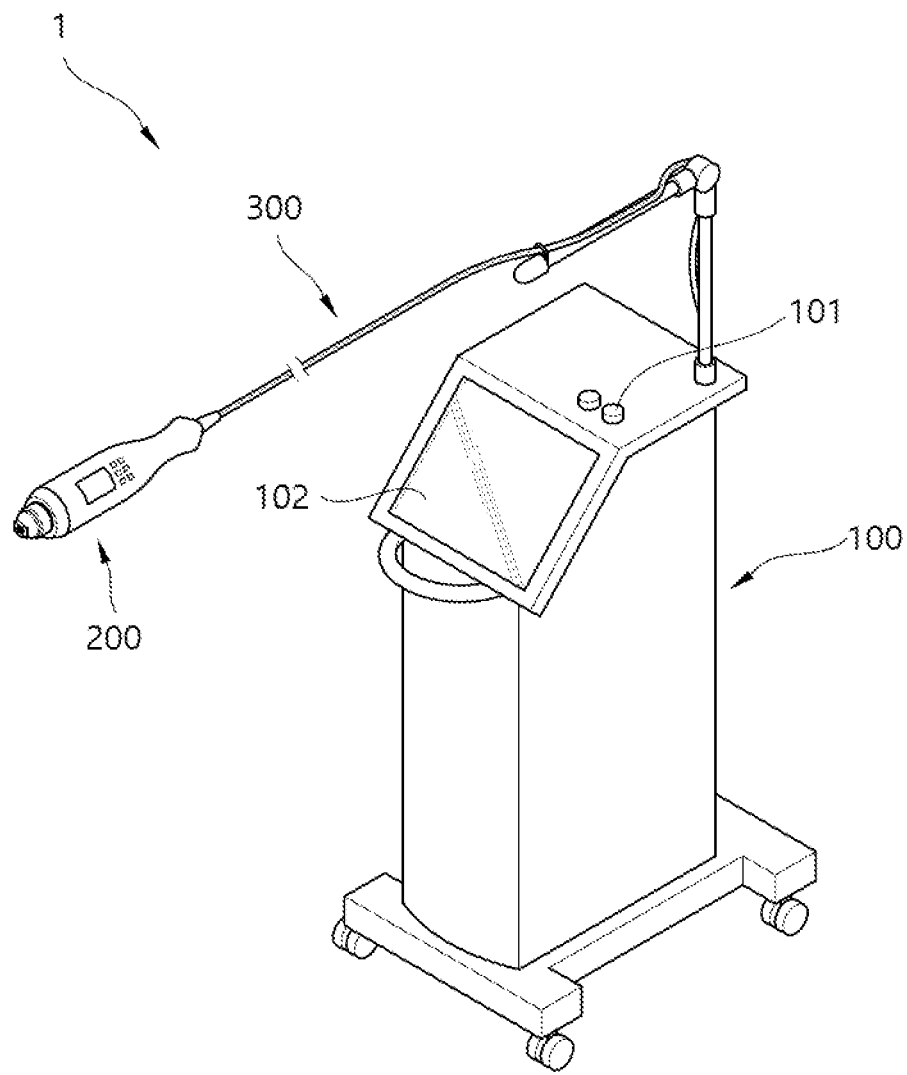
FIG. 1 is a perspective view of a radio frequency (RF) therapeutic device according to an embodiment of the disclosure.

Below, a radio frequency (RF) therapeutic device and a method of controlling the same according to an embodiment of the disclosure will be described in detail with reference to the accompanying drawings. In the following, a relationship between positions of elements will be fundamentally described based on the drawings. For convenience of description, the elements in the drawings may be simplified or exaggerated as necessary. Therefore, the disclosure is not limited to the following description, but may be embodied by adding, modifying or excluding various devices.

Hereinafter, the 'RF therapeutic device' refers to any device for treating mammals including humans. The therapeutic device may include various devices for treatment, which transmit RF energy for the purpose of improving conditions of a lesion or tissue. In the following embodiments, description will be made focusing on a device for treatment of a dermal lesion. However, the disclosure is not limited to these embodiments, but may be applied to various devices used in transferring RF energy to various affected areas, such as a device for surgical treatment of an internal organ lesion.

Hereinafter, the 'tissue' refers to a set of cells that make up various body organs of animals including humans, and includes various tissues that make up various organs in a body, such as dermal tissue.

Hereinafter, the 'insert' refers to an element, which is inserted into tissue, in the therapeutic device. The insert includes various elements, an end portion of which has a sharp, thin and long structure like those of a needle, a micro-needle and a catheter and is inserted up to the inside of tissue by penetrating the surface of the tissue.

Further, an RF circuit will be illustrated and described as simplified focusing on major elements and major factors. Therefore, various circuit elements may be additionally included in the RF circuit besides the illustrated or mentioned elements. However, elements that have relatively little effect or similar effect between control groups will not be described or will be described on the assumption that they have no effects.

Figure 2:
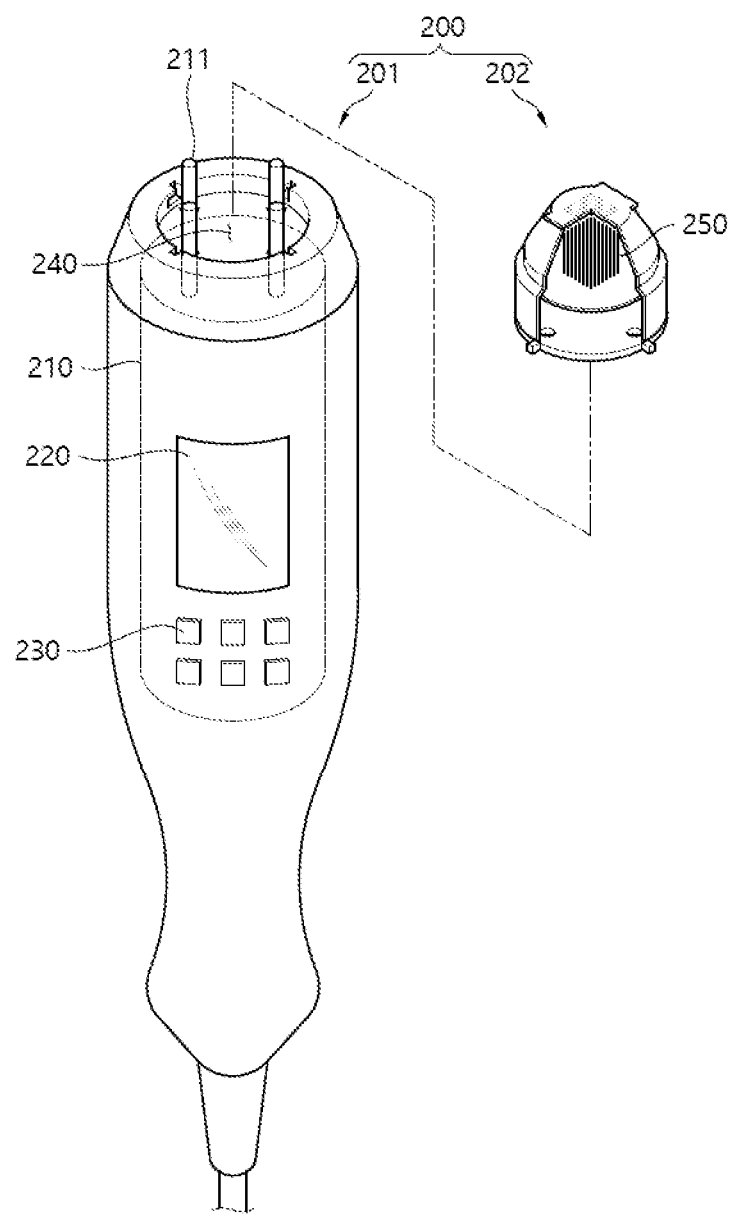
FIG. 2 is a perspective view of a handpiece in the RF therapeutic device of FIG. 1.

Below, a RF therapeutic device according to an embodiment of the disclosure will be described with reference to FIG. 1. FIG. 1 is a perspective view of the RF therapeutic device according to an embodiment of the disclosure, and FIG. 2 is a perspective view of a handpiece in the RF therapeutic device of FIG. 1.

As shown in FIG. 1, the RF therapeutic device according to this embodiment includes a main body 100, and a handpiece 200 to carry out treatment while being gripped by a user.

The main body 100 internally includes an RF generator 110. The RF generator 110 generates RF energy used for treatment. The RF generator 110 may generate the RF energy having various parameters (for example, power, pulse duration, pulse interval, frequency, etc.) according to a patients habitus, treatment purposes, treatment parts, etc. The RF energy generated in the RF generator according to this embodiment is generally used for the purpose of tissue treatment. However, the RF energy may be used for detecting the characteristics of tissue or RF electrodes (to be described later) besides the purpose of tissue treatment. In this regard, detailed descriptions will be made later.

The main body 100 externally includes various switches 101 and a display 102. The switch 101 is configured to control operations of the therapeutic device as well as power on/off, and the display 102 includes a display device to display various pieces of information such as information about operations of the therapeutic device. The display 102 may be embodied by a touch screen configured to not only display various pieces of information but also allow a user to set treatment details in person through the display 102.

The handpiece 200 is connected to the main body 100 by a connector 300. The connector 300 is configured to transmit power, a control signal, etc., required for operating various devices of the handpiece 200 from the main body 100. For example, the connector 300 forms an RF circuit together with the RF generator 110 of the main body 100 and the electrodes of the handpiece 200, and forms a path through which the RF energy generated in the RF generator 110 is transferred to the handpiece 200. Further, information set by a user, information detected during treatment, etc. at one side of the main body and the handpiece are also transmitted to the other side through the connector 300. The connector 300 may be embodied by a cable including various signal lines, power lines, etc. or may be configured to have a curved structure to be easily curved by a users control.

Meanwhile, the handpiece 200 is configured to carry out treatment as disposed at a treatment position, and shaped to be used while being gripped by a user's hand. The handpiece 200 includes an insert 250 to be selectively inserted into tissue to carry out invasive treatment, a driver 210 for moving the insert 250, and a handpiece controller 230 for controlling operation details of the insert 250 and the driver 210.

Specifically, as shown in FIG. 2, the handpiece controller 230 and a handpiece display 220 are provided on an outer surface of a housing 201 of the handpiece 200. The handpiece controller 230 is configured to turn on/off the handpiece 200, adjust an insertion depth of the insert 250, and adjust a level or the like of energy to be transferred through the insert 250. The handpiece display 220 displays various pieces of information needed for treatment to a user. Therefore, a user controls the handpiece controller 230 while gripping the handpiece 200 in his/her hand, thereby carrying out the treatment and at the same time checking the treatment details through the display 220.

The handpiece 200 internally includes the driver 210. The driver 210 is configured to move the insert 250 so that the insert 250 can be selectively inserted into tissue and withdrawn from the tissue. The driver 210 may be embodied using various linear actuators such as a solenoid, hydraulic/pneumatic cylinders, etc., a linear motor, etc. As an example, the driver 210 in this embodiment drives output terminals 211 provided at one side to linearly move in a lengthwise direction. A plurality of needles corresponding to the insert 250 is provided at an end portion of the output terminals 211, and the insert 250 may appear and disappear at one end (one end to be in contact with the treatment position) of the handpiece 200 as the output terminals 211 linearly move.

The insert 250 is, as described above, configured to be inserted up to the inside of the tissue by penetrating the surface of the tissue. The insert 250 in this embodiment is achieved as a microneedle that can be easily inserted in the tissue, but may be embodied to have various structures such as a single needle structure, a catheter, etc. besides the microneedle. Each microneedle in this embodiment has a diameter of 1000 μm or less. Specifically, according to this embodiment, the diameter of the microneedle may range from 100 μm to 500 μm to not only relieve a user's pain when it is inserted, but also minimize damage or bending during the insertion.

Figure 3:
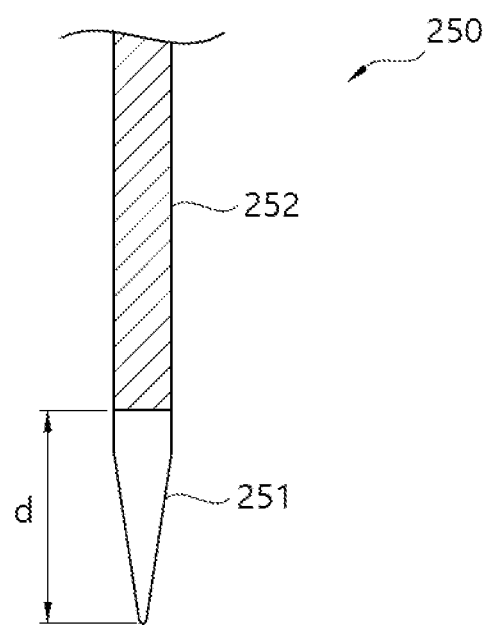
FIG. 3 illustrates a microneedle of FIG. 2.

FIG. 3 illustrates the microneedle of FIG. 2. As shown in FIG. 3, the insert 250 includes a body 252 and an RF electrode 251 formed at an end portion of the body 252. The RF electrode is connected to the RF generator by the foregoing RF circuit, and the RF energy generated in the RF generator is provided to the RF electrodes 251 along the RE circuit. Therefore, the RF electrode 251 transfers the RF energy to the inside of the tissue while being inserted in the tissue. In this case, the exterior of the body 252 includes an insulating material, and the RF electrode includes a conductive material extended from the end portion of the body by a predetermined length d. Here, the length of the RF electrode may range from 0.1 mm to 1 mm, and may also range from 0.2 to 0.7 mm by taking the thickness of a dermal tissue layer into account in the case of skin treatment. The body 252 is internally formed with a conductive path for transferring the RE energy along a lengthwise direction. Therefore, the RF energy transferred to the insert 250 is transferred to the tissue via only the RE electrode 251 provided at the end portion thereof.

In this embodiment, the insert is embodied by a tip module 202 detachably mounted to a handpiece end portion, and replaceable after treatment. The tip module 202 includes a plurality of microneedles to be inserted into a body and a base supporting the plurality of microneedles, and detachably mounted to a recessed portion 240 at one end of the handpiece body. The output terminals 211 are positioned on the rear of the tip module 202, and the plurality of microneedles accommodated in the tip module moves forward/backward as the output terminals 211 moves forward/backward. Further, when the tip module is mounted to the recessed portion 240, the microneedles of the tip module are electrically connected to the RF circuit in the handpiece so that the RF energy can be transferred to the inside of the tissue through the RE electrodes 251 of the microneedles.

Detailed structures of the handpiece and the tip module may be variously embodied with reference to those disclosed in Korean patent publication No. 10-1300123 or the like disclosure. Like this, the insert is detachably provided to thereby prevent infection between patients. Further, various kinds of inserts different in diameter or length may be selectively mounted and used according to treatment details.

Figure 4:
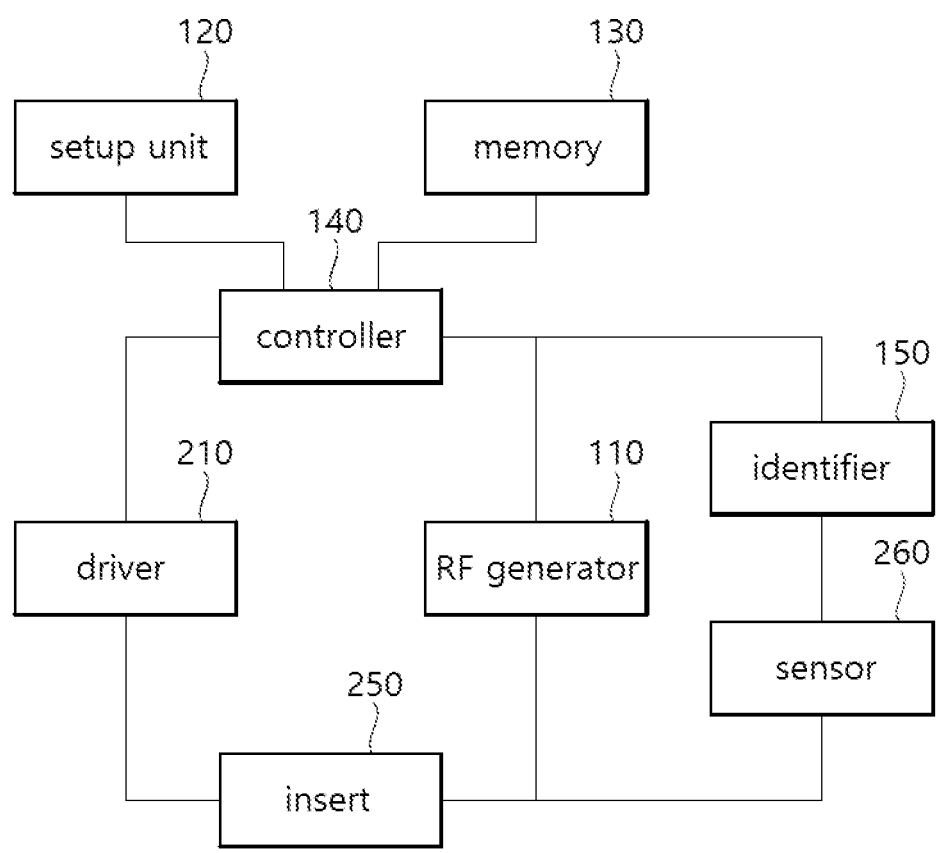
FIG. 4 is a block diagram of a main control system in the RF therapeutic device of FIG. 1.

FIG. 4 is a block diagram of a main control system in the RF therapeutic device of FIG. 1. Below, a control structure of the RF therapeutic device according to an embodiment will be described in detail with reference to FIG. 44.

A controller 140 is configured to control operations of various elements of the main body 100 and the handpiece 200. As shown in FIG. 4, the controller 140 controls the operations of the driver 210, thereby inserting the insert 250 into the tissue, withdrawing the insert 250 from the tissue, and controlling an insertion depth of the insert 250. Further, the controller 140 may control the RF generator 110 to adjust on/off of RF pulses and the parameters of the RF pulses. Thus, the RF therapeutic device 1 can provide RF pulses having appropriate parameters after inserting the microneedles into the tissue.

A setup unit 120 is configured to allow a user to set up a treatment mode and treatment details. Thus, it is possible to set up various details such as the power of the RF energy to be transferred to tissue, the depth of the insert to be inserted into the tissue, the kinds of microneedle to be used, etc. The controller 140 controls various elements to carry out treatment based on settings set up through the setup unit 120. The setup unit 120 may be embodied by the foregoing display and/or switch. Therefore, when various setting options are displayed through the display 102, a user selects the option by touching the display or controlling the switch to thereby change the settings.

Further, the RF therapeutic device 1 additionally includes a memory 130 in which various pieces of data are stored. The controller 140 may store information needed for controlling the RF therapeutic device in the memory 130, or load the stored data from the memory 130 and use the data in control.

Furthermore, the RF therapeutic device 1 additionally includes a sensor 260 and an identifier 150. Here, the sensor 260 measures various parameters of the RF circuit while the RF energy is transferred to body tissue. For example, various RF parameters, such as the power P of the RF energy generated by the RF generator 110, voltage v and current i applied between two electrodes, impedance Z formed between the RF electrodes, variance in impedance of body tissue according to positions, etc. are measured. Further, the identifier 150 identifies characteristics information about the RF electrodes based on the RF parameters measured by the sensor 260. Below, the foregoing configurations of the sensor 260 and the identifier 150 will be described in more detail with reference to the drawings.

Figure 5:
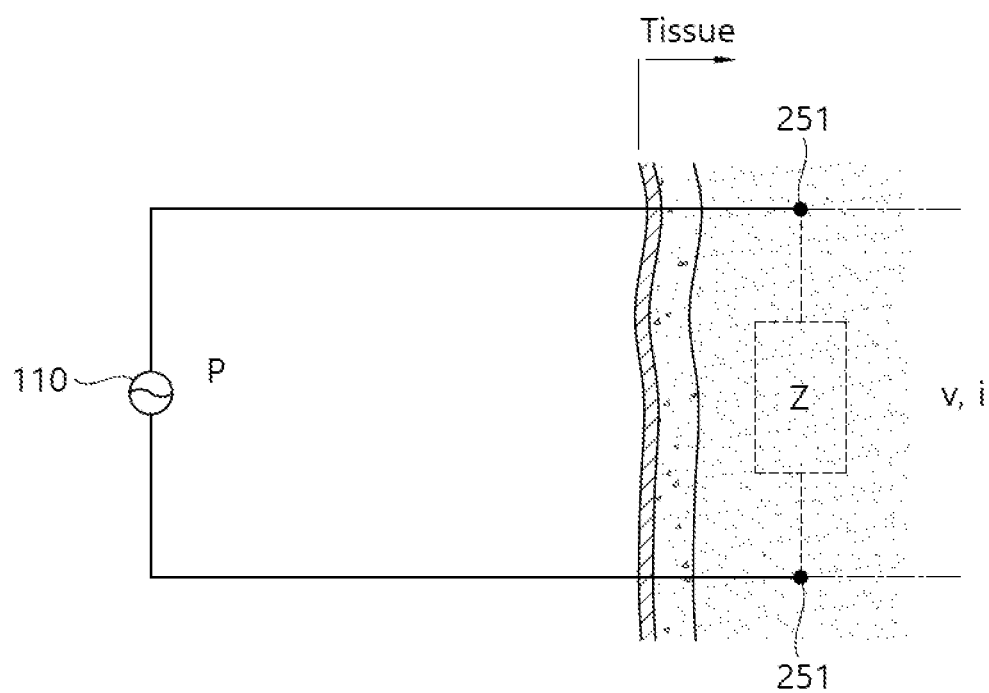
FIG. 5 is a schematic circuit diagram of an RF circuit formed in an RF therapeutic device and tissue during treatment.

FIG. 5 is a schematic circuit diagram of a RF therapeutic device and an RF circuit formed in tissue during treatment. As shown in FIG. 5, the RF energy generated by the RF generator 110 is provided to the RF electrode 251 along an RF circuit, and thus the RF energy is transferred to body tissue while RF current flows through the tissue. In this case, the impedance Z is formed between the RF electrodes 251, and the RF energy is transformed into thermal energy while passing through a path where such impedance Z is formed, and then transferred to the tissue.

Here, the impedance Z between the RF electrodes 251 is varied depending on the RF electrodes' own characteristics and the tissue's characteristics. The impedance refers to characteristics of current conductivity, and is thus affected by the shapes and materials of the RF electrodes and by the components and conditions of the tissue. However, the standardized RF electrodes have conventionally been used in the related art, and therefore the effect due to the characteristics of the tissue rather than the RF electrodes have been mainly taken into account. However, the microneedle has recently been made thinner to relieve a patient's pain and easily inserted into tissue, and therefore thus a level of difficulty in uniformly processing the RF electrodes becomes higher. Accordingly, a processing error, such as difference between the length of the RF electrode (the length of a conductive part in the end portion of the microneedle, d) and a designed length, frequently occurs, thereby causing unexpected variance in impedance.

The impedance is more critically affected by the RF electrodes than by the characteristics of the tissue, and the RF energy transferred to the tissue is largely varied depending on the states of the RF electrodes even though the RF energy is given under the same condition. Accordingly, the therapeutic device according to the disclosure obtains information about the RF electrodes through the sensor 260, and adjusts the parameters of the RF energy through the controller 140 based on the obtained information, thereby solving the foregoing problems.

Referring back to FIG. 4, the sensor 260 measures the impedance Z formed between the RF electrodes while the RF energy is being transferred to body tissue. The impedance may be obtained by measuring the voltage v applied between the RF electrodes and the current i passing through the RF electrodes, and going through operation between the voltage v and the current i. Such obtained impedance Z involves information about the RF electrodes, and the identifier 150 identifies the characteristics of the RF electrodes based on the information (although the obtained impedance includes impedance due to the tissue, the impedance is very little varied depending on the characteristics of the tissue and it is therefore identified that variance in the obtained impedance greater than a preset range is caused by the characteristics of the RF electrodes).

Figure 6:
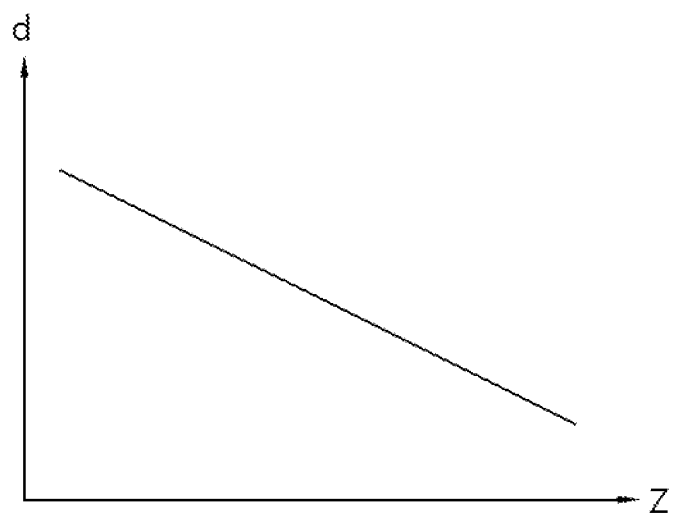
FIG. 6 is a graph showing a relationship between the length of the RF electrode and impedance.

FIG. 6 is a graph showing a relationship between the length of the RF electrode and impedance. As shown in FIG. 6, the length d of the RF electrode is inverse proportion to the impedance Z between the RF electrodes. In other words, the impedance decreases when the RF electrode is long, but increases when the RF electrode is short. This is because the impedance decreases as a contact surface between the RF electrode and the tissue increases.

The memory 130 is configured to store reference impedance information of the RF electrode, and the identifier 150 identifies the characteristics of the RF electrode based on comparison between the reference impedance information stored in the memory 130 and the obtained impedance. In other words, when the obtained impedance is higher than the reference impedance, it is identified that the RF electrode is shorter than a preset length. On the other hand, when the obtained impedance is lower than the reference impedance, it is identified that the RF electrode is longer than the preset length.

The foregoing description shows that difference between the reference impedance and the obtained impedance is affected by the length of the RF electrode, but the difference may be affected by the diameter of the RF electrode, foreign materials contained in the RF electrode, etc. besides the length of the RF electrode. However, it was described that the identifier identifies the length characteristic of the RF electrode because most errors that occur during the processing of the insert are the length error of the RF electrode. Alternatively, the surface areal characteristics or surface characteristics of the RF electrode may be identified.

Further, when the RF therapeutic device is provided to selectively use various kinds of inserts, the memory may be configured to store pieces of reference impedance information respectively corresponding to the kinds of inserts. In this case, the identifier may identify the characteristics of the RF electrode based on comparison with the reference impedance corresponding to the treatment mode set by a user.

Further, FIG. 4 shows a block diagram in which the identifier 150 is branched into the sensor 260 and the controller 140, but this is to distinguish between functions performed in the identifier. Alternatively, the identifier may be provided as a subordinate element of the sensor or as a subordinate element of the controller.

Meanwhile, when the characteristics of the RF electrode are identified, the controller 140 adjusts the parameters of the RF energy based on the identified characteristics of the RF electrode. Although the RF generator 110 supplies the same RF energy, higher impedance between the RF electrodes causes more energy to be transferred to the tissue. Therefore, the controller 140 controls the RF energy to be less transferred to the RF electrodes 251 when the obtained impedance Z is higher than the reference impedance, but controls the RF energy to be more transferred to the RF electrodes 251 when the obtained impedance Z is lower than the reference impedance. Here, the RF energy to be transferred to the RF electrode 251 may be controlled by adjusting the power P of the RF energy generated in the RF generator 110, or may be controlled by adjusting a variable element (not shown) provided on the RF circuit. Further, a degree of increasing or decreasing the RF energy may be controlled in consideration of difference between the obtained impedance and the reference impedance. Under such control, the treatment is uniformly carried out because the controller controls a target level of energy to be transferred even though the RF electrodes are different in characteristics due to the processing error or the like of the RF electrodes.

Further, the memory 130 may further include information about a reference impedance section as well as the set reference impedance corresponding to the RF electrode. Here, the reference impedance section refers to an impedance section where compensation is achieved by the foregoing control for the RF parameters, and it may be identified outside the reference impedance section that the treatment has no substantial effects or it is impossible to carry out the target treatment (for example, the electrode is too short to expect substantial treatment effects, the electrode is so long that the electrode goes beyond a target tissue layer, and so on). Therefore, the controller 140 may show a user that the obtained impedance goes beyond the reference impedance section, and inform the user that the insert is defective. In this case, the controller may control the RF energy not to be transferred to the RF electrode. In this case, the reference impedance section stored in the memory may be varied depending on the set kinds of inserts, and may further be varied depending on treatment parts and treatment details.

As described above, in the RF therapeutic device according to an embodiment, when the sensor 260 obtains information about the RF electrode, the controller 140 adjusts the parameters of the RF energy to be transferred to the RF electrode by taking the obtained information into account, and carries out the treatment based on the adjusted parameters.

In this case, the RF generator 110 may be configured to selectively generate test RF energy for obtaining information about the RF electrode and treatment. RF energy for treating the body tissue. In this case, to carry out the treatment, the controller 140 may control the RF generator 110 to generate the test RF energy at an initial position (i.e., a test position), adjust the parameters of the treatment RF energy when the characteristics of the RF electrode are identified by the test RF energy, and transfer the treatment RF energy to a treatment position based on the adjusted parameters to thereby carry out the treatment.

In this case, the test RF energy may be controlled to have lower power than the treatment RF energy. Because energy higher than expected may be transferred to tissue according to the characteristics of the RF electrode, it may be safe that energy of low power is used in checking the characteristics of the RF electrode. However, without distinguishing between the test RF energy and the treatment RF energy, the treatment RF energy to be transferred to an initial treatment position may be used to identify the characteristics of the RF electrode.

Figure 7:
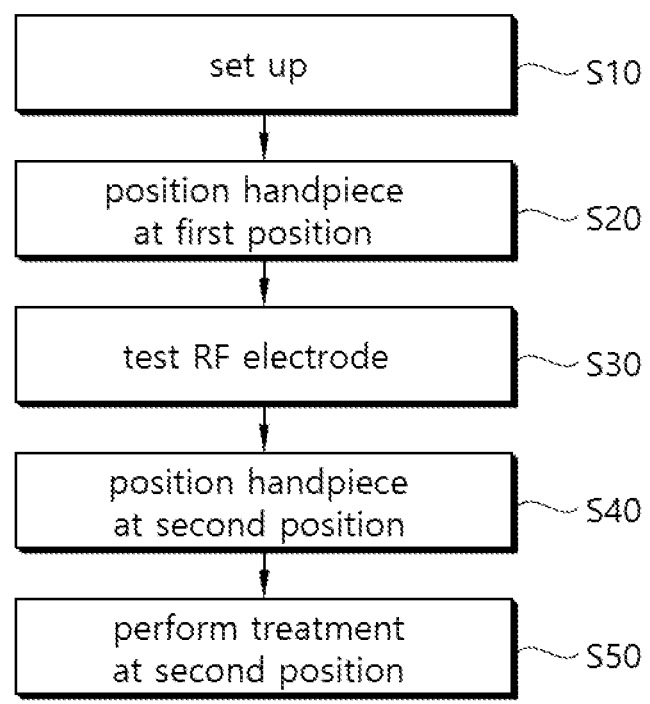
FIG. 7 is a flowchart showing a method of controlling the RF therapeutic device of FIG. 1.
Figure 8:
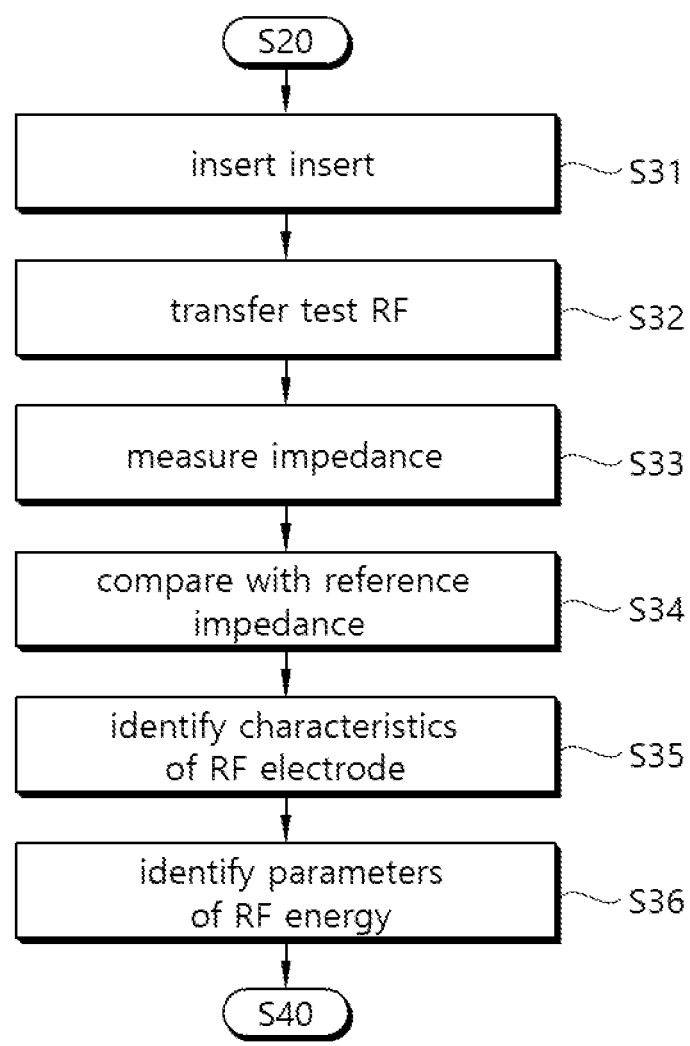
FIG. 8 is a flowchart showing detailed operations of testing the RF electrodes in FIG. 7.

FIG. 7 is a flowchart showing a method of controlling the RF therapeutic device of FIG. 1, and FIG. 8 is a detailed flowchart showing an operation of testing the RF electrodes in FIG. 7. Below, the method of controlling the RF therapeutic device according to an embodiment and the treatment method using the same will be described with reference to FIGS. 7 and 8.

Before carrying out the treatment, a user sets up treatment details through the setup unit 120 (810). In this operation, a user sets up the treatment mode and various parameters in consideration of treatment position, a treatment lesion and a patient's condition. In this operation, the kinds of inserts to be used may be set.

Then, the handpiece is positioned at a first position (S20). The first position may be a separate test position, or may be the first treatment position. Further, a test operation is performed to check the RF electrode information at the first position (S30).

As an initial operation of the test operation, the controller 140 operates the driver 210 to insert the insert 250 into the tissue of the first position in response to a user's control (S31). Further, the controller 140 operates the RF generator 110 to generate the test RF energy, and transfers the RF energy to the body tissue through the RF electrode 251 (S32). In this case, the test RF energy may be set by a user to be, for example, provided having first power.

When the test RF energy is being transferred, the sensor 260 measures the impedance Z formed between the RF electrodes (S33). Such impedance may be obtained by measuring the voltage v applied between the RF electrodes and the current i flowing through the RF electrodes, and going through operation between the voltage v and the current i.

When the sensor 260 measures the impedance, the identifier 150 compares the reference impedance with the measured impedance (S34). Here, the reference impedance may be varied depending on settings set in the setting operation. Further, the characteristics of the RF electrode are identified based on comparison results (S35). For example, when difference between the measured impedance and the reference impedance is greater than or equal to a preset level, it may be identified that a processor error is present. In this case, it may be identified that the length of the RF electrode is shorter than a designed length when the measured impedance is higher than the reference impedance, but longer than the designed length when the measured impedance is lower than the reference impedance.

When the characteristics of the RF electrode 251 are identified through the foregoing operations, the controller 140 identifies the parameters of the RF energy based on the identified characteristics (S36). In this case, the parameters for the RF energy to be adjusted may be parameters for the treatment RF energy. For example, when the power of basic treatment RF energy based on the treatment mode set in the setting operation is second power, the controller 140 may adjust the power of the treatment RF energy into third power based on a detection result of the sensor 260. Specifically, when the measured impedance is higher than the reference impedance, the third power may be adjusted to be lower than the second power. On the other hand, when the measured impedance is lower than the reference impedance, the third power may be adjusted to be higher than the second power. Here, the power of the treatment RF energy generated in the RF generator is adjusted by way of example. Alternatively, the parameters of the variable element on the RF circuit may be identified so that the level of energy to be transferred to the tissue through the electrode can be adjusted when the treatment RF energy is transferred However, when the measured impedance is equal to the reference impedance or has an error within an allowable range in the foregoing operation, the controller 140 may keep the settings (i.e., the second power) of the treatment RF energy without adjusting the parameters.

When the operation of testing the RF electrode is completed through the foregoing operation, the handpiece is moved to a second position (S40). The second position refers to a position corresponding to a treatment region, and the treatment operation is carried at the corresponding position (S50). In the treatment operation, the insert 250 is inserted in the second position like the operation S31, and then the treatment RF energy is transferred to the corresponding position. In this case, the parameters of the treatment RF energy to be transferred are parameters identified through the test operation.

When the treatment operation is completed with respect to the second position through the foregoing operations, a user moves the handpiece and carries out the treatment with respect to the other treatment positions based on the parameters identified in the operation S30 like the operations S40 and S50.

According to an additional embodiment, while the treatment is carried out with respect to the other treatment positions such as the second position, the RF energy may be controlled to be adjusted in consideration of the impedance according to the characteristics of tissue in each individual position. In this case, the parameters identified in the operation S30 are used in transferring the treatment RF energy. However, the parameters (e.g., a width of an RF pulse) may be slightly changed and controlled at the corresponding position based on a result of tissue impedance measured in real time As described above, a therapeutic device according to an embodiment has advantages that treatment is stably carried out even though the RF electrodes have a processing error or the like because parameters of treatment energy are adjusted based on identified characteristics of the RF electrodes.

With such features of the disclosure, even when a user mounts a different kind of insert other than a set insert by mistake in a case where various kinds of inserts are selectively mountable to carry out treatment as well as a case where the RF electrodes involve a processing error, the characteristics of the mounted RF electrode are identified and the controller controls RF parameters to be adjusted in consideration of the identified characteristics.

Embodiments of the disclosure have been described above in detail, but the disclosure is not limited to these embodiments. It will be appreciated by a person having ordinary skill in the art to which the disclosure pertains that various changes or modifications can be made in these embodiments without departing from the scope of technical features of the disclosure defined in the appended claims.

The invention claimed is:

1. A radio frequency (RF) therapeutic device comprising:
   an RF generator configured to generate RF energy;
   an insert formed with an RF electrode at an end portion thereof, and configured to be selectively inserted in body tissue and transfer the RF energy to the body tissue;
   a sensor configured to measure impedance while the RF energy is being transferred to the body tissue and determine information about an electrical characteristic of the RF electrode; and
   a controller configured to compensate for a processing error of the insert by adjusting parameters of the RF energy based on a determined result of the sensor.

2. The RF therapeutic device according to claim 1, wherein the controller is configured to compare the measured impedance with reference impedance corresponding to the RF electrode, and adjust the parameters of the RF energy based on a comparison result.

3. The RF therapeutic device according to claim 2, wherein the controller is configured to control the RF energy transferred to the RF electrode to be decreased when the measured impedance is higher than the reference impedance, but control the RF energy transferred to the RF electrode to be increased when the measured impedance is lower than the reference impedance.

4. The RF therapeutic device according to claim 1, wherein the controller is configured to inform a user that the insert is defective when the measured impedance goes beyond a reference impedance section for the RF electrode.

5. The RF therapeutic device according to claim 4, wherein the controller is configured to control the RF energy not to be transferred to the RF electrode when the measured impedance goes beyond the reference impedance section for the RF electrode.

6. The RF therapeutic device according to claim 1, further comprising an identifier configured to identify length information about the RF electrode based on impedance measured by the sensor.

7. The RF therapeutic device according to claim 1, wherein the RF generator is configured to selectively generate test RF energy used in determining information about the RF electrode and treatment RF energy used in treating body tissue.

8. The RF therapeutic device according to claim 7, wherein the controller is configured to identify parameters of the treatment RF energy based on impedance information detected by transferring the test RF energy at an initial insertion position, and control the RF generator to transfer the treatment RF energy having the identified parameters to at a subsequent insertion position.

9. The RF therapeutic device according to claim 7, wherein the test RF energy comprises lower power than the treatment RF energy.

10. The RF therapeutic device according to claim 1, wherein the insert is replaceably provided, and the controller is configured to identify whether the insert matches a set model based on a detection result of the sensor.

11. The RF therapeutic device according to claim 1, wherein the insert comprises a plurality of microneedles, each microneedle comprises a body comprising an insulating material on a surface thereof, and the RF electrode comprises a conductive material formed at an end portion of the body.

12. The RF therapeutic device according to claim 11, wherein the microneedle comprises a cross-sectional diameter of 100 to 500 μm, and the electrode portion comprises a length of 0.1 to 1 mm.

13. A method of controlling a radio frequency (RF) therapeutic device, comprising:
   positioning a handpiece at a first position;
   inserting an insert into body tissue at the first position and transferring RF energy;
   determining information about an electrical characteristic of an RF electrode by measuring impedance while the RF energy is being transferred;
   identifying parameters of the RF energy based on the determined information to compensate for a processing error of the insert;
   positioning the handpiece at a second position; and
   transferring the RF energy comprising the identified parameters.

14. The method of claim 13, wherein the identification of the parameters of the RF energy comprises comparing the measured impedance with reference impedance corresponding to the RF electrode, and identifying the parameters of the RF energy based on a comparison result.

15. The method of claim 13, further comprising decreasing output parameters of the RF energy transferred to the RF electrode when the measured impedance is higher than the reference impedance, but increasing output parameters of the RF energy transferred to the RF electrode when the measured impedance is lower than the reference impedance.

16. The method of claim 13, wherein
   the RF energy transferred to the first position comprises test RF energy, and the RF energy transferred to the second position comprises treatment RF energy, and
   the test RF energy comprises lower power than the treatment RF energy.

17. The method of claim 13, wherein
   the determination of the information about the RF electrode by measuring impedance while the RF energy is being transferred comprises identifying length information about the RF electrode, and
   the parameters of the RF energy are identified based on the length information of the RF electrode.

18. A therapeutic method of using a radio frequency (RF) therapeutic device, comprising:
   positioning a handpiece at a first position;
   inserting an insert into body tissue at the first position and transferring RF energy;
   determining information about an electrical characteristic of an RF electrode by measuring impedance while the RF energy is being transferred;
   identifying parameters of the RF energy based on the determined information to compensate for a processing error of the insert;
   positioning the handpiece at a second position; and
   carrying out treatment by inserting the insert into body tissue at the second position and transferring the RF energy comprising the identified parameters.

19. The method of claim 18, wherein the identification of the parameters of the RF energy comprises comparing the measured impedance with reference impedance corresponding to the RF electrode, and identifying the parameters of the RF energy based on a comparison result.

20. The method of claim 18, wherein
the RF energy transferred to the first position comprises test RF energy, and the RF energy transferred to the second position comprises treatment RF energy, and
the test RF energy comprises lower power than the treatment RF energy.

\* \* \* \* \*